US008546315B2

(12) United States Patent
Macias

(10) Patent No.: US 8,546,315 B2
(45) Date of Patent: Oct. 1, 2013

(54) HIGH QUALITY BAR SOAP INCORPORATING TRICLINIC TALC

(75) Inventor: Jesus Macias, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 13/161,128

(22) Filed: Jun. 15, 2011

(65) Prior Publication Data

US 2012/0322711 A1 Dec. 20, 2012

(51) Int. Cl.
*A61K 8/00* (2006.01)

(52) U.S. Cl.
USPC ........... 510/141; 510/152; 510/155; 510/481; 510/485

(58) Field of Classification Search
USPC ........................................................ 510/141
See application file for complete search history.

(56) References Cited

U.S. PATENT DOCUMENTS

| | | | | |
|---|---|---|---|---|
| 3,965,241 | A | 6/1976 | Baak et al. | |
| 5,229,094 | A | 7/1993 | Clauss et al. | |
| 5,401,482 | A | 3/1995 | Clauss et al. | |
| 5,849,333 | A | 12/1998 | Nordhauser et al. | |
| 2008/0125340 | A1* | 5/2008 | Dail | 510/130 |
| 2011/0143984 | A1* | 6/2011 | Yang et al. | 510/151 |

OTHER PUBLICATIONS

Rayner et al, "The Crystal Structure of Talc", Clays and Clay Minerals, 1973, vol. 21, pp. 103-114.

* cited by examiner

*Primary Examiner* — Necholus Ogden, Jr.
(74) *Attorney, Agent, or Firm* — David K. Benson

(57) ABSTRACT

A personal cleansing composition includes soap at a concentration of at least 10 weight percent of the composition; and talc having a primarily triclinic crystal structure, the talc being included at a concentration of between 0.1 and 15 weight percent of the composition. A method for enhancing lathering properties of a bar soap includes the step of molding a bar soap from such a composition.

14 Claims, 2 Drawing Sheets

HIGH QUALITY BAR SOAP INCORPORATING TRICLINIC TALC

FIELD OF THE INVENTION

The present invention generally relates to bar soap products, and more particularly relates to personal cleansing bar soap products that include ingredients for improving lather and skin feel benefits.

BACKGROUND OF THE INVENTION

Personal care compositions such as solid soaps are of course well known. Toilet soaps in bar form are usually formulated with a variety of additives to provide benefits that are not inherent in the soap itself. Additives may be employed to, for example, enhance the lathering of the soap, to enhance the mildness of the soap, or to enhance its antibacterial effectiveness. Additionally, various additives, such as talc, may be employed to reduce cost and provide various benefits to the user.

Commercial soap bars conventionally comprise one or more "soaps," which, for purposes of describing this component of the compositions of the present invention, have the meaning as normally understood in the art monovalent salts of monocarboxylic fatty acids. The counterions of the salts generally include sodium, potassium, ammonium and alkanol ammonium ions, but may include other suitable ions known in the art. The soap bars may also include optional adjuvant ingredients such as moisturizers, humectants, antibacterials, water, fillers, polymers, dyes, and fragrances.

Typically, the soap components in conventional soap bars comprise salts of long chain fatty acids having chain links of the alkyl group of the fatty acids from about 8 carbon atoms, to about 20 carbon atoms in length. The particular length of the alkyl chain of the soaps is selected for various reasons including cleansing capability, lather capability, and cost.

As previously mentioned, talc is one agent that provides various user benefits. For example, talc imparts increased lather and improved skin feel to a user when it is employed in a bar of soap. Furthermore, since talc is a useful and inexpensive filler it decreases the cost of manufacturing soap bars while providing such user benefits. Enhancing these benefits in a cost-effective manner is an aim for soap companies.

Accordingly, there is a continuing need for optimizing bar soap formulations in terms of their user benefits such as skin feel and the amount of lather generated while washing with a typical amount of soap. In addition, it is desirable to provide such benefits with as little expense as possible. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A personal cleansing composition is provided in solid form. The personal cleansing composition includes soap at a concentration of at least 10 weight percent of the composition; and talc having a primarily triclinic crystal structure, the talc being included at a concentration of between 0.1 and 15 weight percent of the composition.

A method is also provided for enhancing lathering properties of a bar soap. The method includes the step of molding a bar soap from a composition including soap at a concentration of at least about 10 weight percent of the composition, and talc having a primarily triclinic crystal structure, the talc being included at a concentration of between about 0.1 and about 15 weight percent of the composition.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

Figure 1:
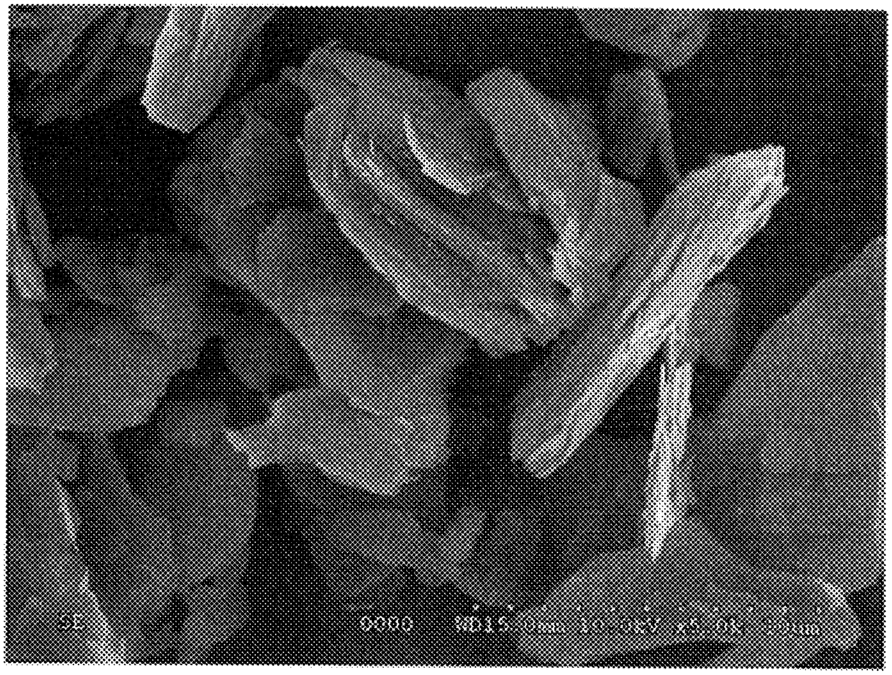
FIG. 1 is a scanning electrode microscope (SEM) image of talc having a primarily monoclinic crystal system.

The following detailed description of the invention is merely exemplary in nature and is not intended to limit the invention or the application and uses of the invention. Furthermore, there is no intention to be bound by any theory presented in the preceding background of the invention or the following detailed description of the invention.

The personal cleansing bars of the present invention typically, although not as a requirement, will include the components outlined in Table 1, with the listed concentration ranges being after manufacture and in the final product form. The bars may contain additional additives, such as antibacterial agents, dyes, perfumes, polymers, silicones, encapsulated materials, and the like.

TABLE 1

| Ingredient | Range (wt. %) | Preferred (wt. %) | Most Preferred (wt. %) |
|---|---|---|---|
| water-soluble polyhydric solvent(s) | 15-65 | 25-65 | 35-55 |
| $3^+$-OH, e.g., glycerine, sugar alcohols | 5-35 | 10-30 | 15-25 |
| 2-OH, e.g., propylene glycol, polyethylene glycol, dipropylene glycol | 10-30 | 15-20 | 20-30 |
| soap(s) | 10-80 | 20-75 | 50-75 |
| non-soap surfactant(s) | 1-25 | 2-15 | 2-10 |
| talc | 0.1-15 | 1-10 | 3-8 |
| water | 4-20 | 8-16 | 10-15 |

The preparation of toilet soap bars, as is well known by those skilled in soap manufacture, typically involves the use of water-soluble soap from a fat charge that is capable of providing a combination of individual soaps of fatty acids suitable for the formation of a solid bar. Individual soap compounds may be alkali metal, ammonium or substituted ammonium salts, preferably sodium or potassium salts, of long-chain fatty acids. Normally such fatty acids will be straight chain saturated or unsaturated fatty acids of from 8 to 24 carbon atoms, preferably from 14 to 18 carbon atoms. Suitable fatty acids are those of tallow, groundnut, cottonseed, palm, palm kernel, babassu, and coconut oils, for instance lauric, myristic, palmitic, oleic, and stearic acids and the acids of dehydrated hardened castor oil; or erucic and behenic acids. An exemplary insoluble fatty acid soap is at least 90% by weight, more preferably at least 95% by weight selected from the group consisting of sodium myristate, sodium palmitate, sodium stearate, sodium cocoate, sodium palm kernalate, sodium tallowate, and mixtures of any two or more thereof.

The non-soap surfactant(s) can be at least one anionic surfactant, cationic surfactant, nonionic surfactant, amphoteric surfactant or a compatible mixture of anionic, cationic, nonionic and/or amphoteric surfactants.

Suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263-266, incorporated herein by reference. Numerous other anionic surfactants, and classes of anionic surfactants, are disclosed in Laughlin et al. U.S. Pat. No. 3,929,678, incorporated herein by reference.

The cleansing bars of the present invention also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, and mixtures thereof. Fatty alcohol ethoxylates (FAE) are useful for dissolving antibacterial compounds, such as triclosan or triclocarban (TCC).

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof. Numerous other nonionic surfactants are disclosed in McCutcheon's Detergents and Emulsifiers, 1993 Annuals, published by McCutcheon Division, MC Publishing Co., Glen Rock, N.J., pp. 1-246 and 266-272; in the *CTFA International Cosmetic Ingredient Dictionary, Fourth Ed*., Cosmetic, Toiletry and Fragrance Association, Washington, D.C. (1991) (hereinafter the CTFA Dictionary) at pages 1-651; and in the *CTFA Handbook*, at pages 86-94, each incorporated herein by reference.

In addition to anionic and nonionic surfactants, cationic, amphoteric, and amphoteric surfactants can be used in the cleansing bars of the present invention. Examples of cationic surfactants include amine oxides.

Amphoteric surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)-propane-1-sulfonate, sodium 2-(dodecylamino)ethyl sulfate, sodium 2-(dimethylamino) octadecanoate, disodium 3-(N-carboxymethyl-dodecylamino) propane-1-sulfonate, disodium octadecyliminodiacetate, sodium 1-carboxymethyl-2-undecylimidazole, sodium N,N-bis(2-hydroxyethyl)-2-sulfato-3-dodecoxypropylamine, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

The personal cleansing bars may also include a combination of water-soluble polyhydric organic solvents including about 5% to about 35% by weight water-soluble polyhydric solvent(s) having three or more hydroxyl groups ($3^+$-OH). Exemplary personal cleansing bars also include about 10% to about 30% by weight polyhydric solvent(s) having two hydroxyl groups (2-OH). Preferred water soluble organic polyols having two hydroxyl groups (2-OH) include propylene glycol, dipropylene glycol, butylene glycol, ethylene glycol, 1,7-heptanediol, monoethylene glycols, polyethylene glycols, polypropylene glycols of up to 8,000 molecular weight, mono-$C_{1-4}$ alkyl ethers of any of the foregoing, and mixtures thereof. Preferred water-soluble polyhydric solvents that have at least three hydroxyl groups ($3^+$-OH) include glycerine, and any sugar alcohol, such as sorbitol.

Examples of suitable sugar alcohols include tetritols such as erythritol, threitol, D-threitol, L-threitol, and D,L-threitol; pentitols such as ribitol, arabinitol, D-arabinitol, L-arabinitol, D,L-arabinitol and xylitol, hexitols such as allitol, dulcitol (galacitol), glucitol, sorbitol, (D-glucitol), L-glucitol, D,L-glucitol, D-mannitol, L-mannitol, D,L-mannitol, altritol, D-altritol, L-altritol, D,L-altritol, iditol, D-iditol, and L-iditol; and disaccharide alcohols such as maltitol, lactitol and isomalt.

The personal cleansing bars of the present invention may optionally include one or more monohydric alcohols. If present, such alcohols are provided at a concentration preferably no greater than about 4 percent by weight, and most preferably no greater than about 2 percent by weight.

The personal cleansing bars of the present invention may contain optional ingredients well known to persons skilled in the art. Such optional ingredients typically are present, individually, from 0% to about 5%, by weight, of the composition, and, collectively, from 0% to about 20%, by weight, of the composition. Classes of optional ingredients include, but are not limited to, dyes, fragrances, pH adjusters, thickeners, fillers, viscosity modifiers, buffering agents, foam stabilizers, antioxidants, foam enhancers, chelating agents, opacifiers, sanitizing or anti-microbial agents, preservatives, polymers, silicones, vitamin E or other vitamins, herb extracts, encapsulated materials, and similar classes of optional ingredients known to persons skilled in the art.

Specific classes of optional ingredients include alkanolamides as foam boosters and stabilizers; gums and polymers as thickening agents; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

The addition of talc to personal cleansing bars, in accordance with various embodiments of the present invention, results in user perceived benefits such as freshness, smoothness, lather generation and creaminess. Additionally, aspects relating to fragrance retention, deposition and the amounts perceived are improved. Further still the addition of talc may result in substantial costs savings.

As appearing herein, the term "talc" denotes a composition consisting entirely or almost entirely of hydrated magnesium silicate. Talc may generally be described by either of the following formulas $H_2Mg_3(SiO_3)_4$ or $Mg_3Si_4O_{10}(OH)_2$, with theoretically 31.7% MgO, 63% $SiO_2$, and 4.8% $H_2O$ by weight. Other very minor elements and impurities may be included in the general talc crystal structure as well. Preferably, talc in the form of talcum powder is utilized. Talc is conventionally preferred as a filler in soap bar products due, at least in part, to its lubricating effects and to its ability to increase the overall moisture content of the personal care cleansing composition. The addition of talc results in enhancement of a number of skin feel characteristics (e.g., the production of noticeably creamier lather). Without intending to be bound by theory, this is believed to be the result of an increase in the surface area of the personal care composition, in bar form, when granules of talc are separated from the bar thus producing tiny cavities in the bar's outer surface into which water may flow.

Talc has a primarily monoclinic crystal lattice system, and FIG. 1 is a scanning electrode microscope (SEM) image of talc that has a primarily monoclinic crystal system. In crystallography, the monoclinic lattice system is one of the seven lattice point groups. A crystal system is described by three vectors. In the monoclinic system the crystal is described by vectors of unequal length. They form a rectangular prism with a parallelogram as its base. Thus, two pairs of vectors are perpendicular, while the third pair makes an angle other than 90°.

Figure 2:
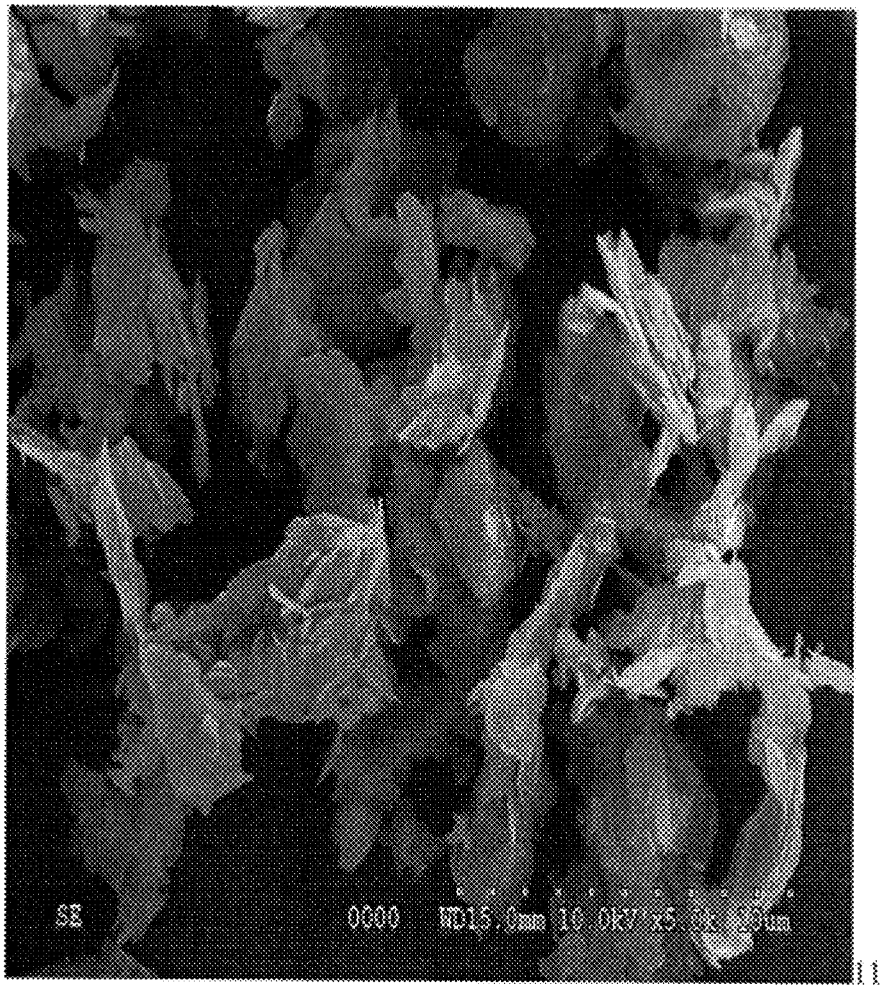
FIG. 2 is a SEM image of talc having a primarily triclinic crystal system used in a bar soap according to an embodiment of the present invention.

In contrast, in a triclinic crystal system is another of the seven lattice point groups and is also described by three basis vectors in which the crystal has vectors of unequal length, but in the triclinic system all three vectors are not mutually orthogonal. It is the only lattice type that has no mirror planes. FIG. 2 is a SEM image of talc having a primarily triclinic crystal system.

To better understand the structure and efficacy of talc when used in solid soap formulations, six talc samples from various quarries in different global loci were analyzed to determine their respective amounts of transition metals. None of the samples contained any trace of cobalt, and one included 25 ppm copper. All six samples contained iron, and the iron concentration in each varied between 209 and 1116 ppm.

Separate bar soap formulations were prepared, with each bar including one of the six talc samples that were analyzed for transition metal content. The finished soap products were evaluated for color stability as well. After twelve weeks of being stored in identical conditions, one bar exhibited color improvement when compared with a control bar. The bar with improved color had a similar amount of iron when compared with the control bar. Both bars were further evaluated for their chemical composition and their talc crystallography. One surprising finding from the analyses was that the bars had similar chemical compositions but had different talc crystallography. The control bar had monoclinic talc, while the bar with improved color stability had talc with a primarily triclinic crystal structure. Testing reveals that soap bars with primarily triclinic talc exhibit improved whiteness that is sustained over a longer period of time than bars having monoclinic talc.

Consumer testing performed on the control bar and the triclinic talc bar also revealed some surprising attributes for the triclinic talc bar. The bars were tested and rated based on attributes including overall liking of the bar, overall lather liking, ease of lathering, skin feel during washing, creaminess of lather while washing, ease of rinsing, and the amount of lather generated. For all of these attributes, the triclinic talc bar rated significantly higher than the control bar despite the fact that the two bars were identical in their formulations apart from the type of talc used in each bar. The greatest disparities between the two bars were produced in the attributes of ease and amounts of lather generation, overall lather liking, and lather creaminess.

By way of illustration and not of limitation, the formulation of one exemplary personal cleansing composition is set forth in the following table.

| Component | Weight % |
|---|---|
| Sodium Soap | 71.5 |
| Water | 12.1 |
| Free Fatty Acid | 5.0 |
| Talc (primarily triclinic) | 5.0 |
| Perfume | 1.4 |

-continued

| Component | Weight % |
|---|---|
| Glycerin | 0.9 |
| Dye(s) | 0.016 |
| Other (e.g., salt, antimicrobial, etc.) | 4.084 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is

1. A personal cleansing composition in solid form, comprising:

soap at a concentration of at least about 10 weight percent of the composition; and talc having a primarily triclinic crystal structure, the talc being included at a concentration of between about 0.1 and about 15 weight percent of the composition.

2. The composition according to claim 1, further comprising:

a polyhydric solvent at a concentration of at least 15 weight percent of the composition.

3. The composition according to claim 1, wherein the soap is included in the composition at a concentration ranging between about 20 and about 75 weight percent.

4. The composition according to claim 1, wherein the soap is included in the composition at a concentration ranging between about 50 and about 75 weight percent.

5. The composition according to claim 1, further comprising:

a non-soap surfactant at a concentration ranging between about 1 and about 25 weight percent.

6. The composition according to claim 2, wherein the polyhydric solvent has at least three hydroxyl groups and is included in the composition at a concentration ranging between about 5 and about 35 weight percent.

7. The composition according to claim 2, wherein the polyhydric solvent has two hydroxyl groups and is included in the composition at a concentration ranging between about 10 and about 30 weight percent.

8. A method of enhancing lathering properties of a bar soap, comprising:

molding a bar soap from a composition comprising soap at a concentration of at least about 10 weight percent of the composition, and talc having a primarily triclinic crystal structure, the talc being included at a concentration of between about 0.1 and about 15 weight percent of the composition.

9. The method according to claim 8, wherein the composition used in the step of molding the bar soap further comprises a polyhydric solvent at a concentration of at least 15 weight percent of the composition.

10. The method according to claim 8, wherein the soap in the composition used in the step of molding the bar soap is included in the composition at a concentration ranging between about 20 and about 75 weight percent.

11. The method according to claim 8, wherein the soap in the composition used in the step of molding the bar soap is included in the composition at a concentration ranging between about 50 and about 75 weight percent.

12. The method according to claim 8, wherein the composition used in the step of molding the bar soap further comprises a non-soap surfactant at a concentration ranging between about 1 and about 25 weight percent.

13. The method according to claim 9, wherein the polyhydric solvent in the composition used in the step of molding the bar soap has at least three hydroxyl groups and is included in the composition at a concentration ranging between about 5 and about 35 weight percent.

14. The method according to claim 9, wherein the polyhydric solvent in the composition used in the step of molding the bar soap has two hydroxyl groups and is included in the composition at a concentration ranging between about 10 and about 30 weight percent.

* * * * *